United States Patent [19]

Bechai et al.

[11] 4,417,583

[45] Nov. 29, 1983

[54] APPARATUS AND METHOD OF INTERNAL EXAMINATION OF GASTRO INTESTINAL TRACT AND ADJACENT ORGANS

[76] Inventors: Nabil R. Bechai, 65 Knighton Dr., Toronto, Ontario, Canada, M4A 1V9; Alan J. Cousin, 186 Johnston Ave., Toronto, Ontario, Canada, M2N 1H3

[21] Appl. No.: 393,938

[22] Filed: Jun. 30, 1982

Related U.S. Application Data

[63] Continuation of Ser. No. 135,391, Mar. 31, 1982, abandoned.

[51] Int. Cl.$^3$ .............................................. A61B 10/00
[52] U.S. Cl. ......................................... 128/660; 128/4
[58] Field of Search ............................. 128/660–663, 128/24 A, 4, 6; 73/623, 642

[56] References Cited

U.S. PATENT DOCUMENTS

| | | | |
|---|---|---|---|
| 3,055,210 | 9/1962 | Joy | 73/644 X |
| 3,556,079 | 1/1971 | Omizo | 128/661 |
| 3,779,234 | 12/1973 | Eggleton et al. | 128/660 |
| 3,817,089 | 6/1974 | Eggleton et al. | 128/661 |
| 3,938,502 | 2/1976 | Bom | 128/660 |
| 4,349,032 | 9/1982 | Koyata | 128/4 X |

FOREIGN PATENT DOCUMENTS

| | | | |
|---|---|---|---|
| 2305501 | 8/1974 | Fed. Rep. of Germany | 128/660 |
| 2758040 | 6/1979 | Fed. Rep. of Germany | 128/660 |
| 54-1984 | 1/1979 | Japan | 128/660 |
| 387698 | 9/1973 | U.S.S.R. | 128/660 |

OTHER PUBLICATIONS

Resnick, M. I. et al. "Ultrasonography of the Urinary Bladder, Sem. Vesicles and Prostate", UTS in Urology by Resnick & Sanders, Wims & Williams Publ. Balt. 1979, pp. 220–224.

Wells, M. K. et al., "UTS Pulsed Doppler Trans-Esophageal Meas. Aortic Haemodynamics", *Ultrasonics* Sep. 1979.

Lutz, H. et al., "Transgastrophic Ultrasonography", *Endoscopy* vol. 8, 1976.

Fleischer, A. C. et al., "Sonographic Patterns of Distended, Fluid-Filled Bowel", *Radiology* vol. 133, Dec. 1976.

Hisovoga, K. et al. "A New Real-Time Sector Scouring System", *UTS in Medicine* vol. 4.

Taylor, W. B. et al., "High Resolution Trans-Rectal UTS System", *Med. in Biology* vol. 5, 1979.

Primary Examiner—Kyle L. Howell
Assistant Examiner—Francis J. Jaworski
Attorney, Agent, or Firm—Hirons, Rogers & Scott

[57] ABSTRACT

A probe for use in internally examining a gastro intestinal tract and adjacent organs includes a head connected to an elongate body portion. A plurality of ultrasonic crystals are spaced around the periphery of the head and the crystals are controlled to produce a real time scan of the tract which may be viewed or recorded. Fluid is delivered through lumens in the body portion to the external surface of the head to couple acoustically the crystals and wall of the tract. A see-head crystal array is provided on the probe to enable the head to be maneuvered within the tract. The probe is used to provide a method of internal examination which includes inserting the probe into the tract, energizing the crystals and acoustically coupling the crystals to the tract by supplying a fluid to the tract in the region of the head of the probe.

8 Claims, 3 Drawing Figures

APPARATUS AND METHOD OF INTERNAL EXAMINATION OF GASTRO INTESTINAL TRACT AND ADJACENT ORGANS

The present application is a continuation of application Ser. No. 135,391, filed 3-31-82, now abandoned.

The present invention relates to examination apparatus and to methods of using such apparatus. In particular the invention relates to apparatus and a method for internally examining a gastro intestinal tract.

Various methods and devices are known for obtaining information relating to the gastro intestinal tract.

The most popular of available methods for examining the G.I. tract is a Barium-based X-ray technique. This consists of the introduction of Barium into the tract which makes it radiopaque. Pathology is then indicated indirectly by changes in the lining which is outlined by fluoroscopy and on several X-rays. Both X-rays and fluroscopy involve exposure of the corresponding portions of the patient to significant amounts of ionizing radiation. Aside from the radiation hazard to both patient and examiner, the major disadvantage is that a definitive diagnosis is difficult to make in many cases because the information obtained is only indirect.

An alternate method has resulted from advances made in the field of fiber optics. Here, a small diameter probe containing the fiber optics is inserted into the G.I. tract. By appropriate maneuvers, an experienced physician is able to visualize the lining of the tract. Although there is no radiation hazard associated with this technique, several limitations are still present. The physician is again only able to visualize the lining of the tract. Further, the field of view is very limited and stems from physical limits of characteristics of fibre optic systems. Both limitations detract from the efficacy of detecting pathologies.

One immediate result of the limited field of view is that some lesions can be missed dependent on the skill of the physician. In addition, no record of the examination is made which implies that discussion with others based on what was seen is not possible and no visual images of the examination are available for further reference.

The present invention involves the insertion of a probe similar in size to a fiber optic probe that is acoustically coupled to the G.I. tract with an appropriate fluid medium. The probe has the electroacoustic capability of providing a three-dimensional view of the structures surrounding the transducer. This means that the complete image is obtained without requiring mechanical rotations of the transducer within the patient.

If desirable, a method for locating the spatial position of the probe within the body is available. In this way, the location from which the calibrated image is obtained may be determined. From these images, diagnosis and location of lesions within the G.I. tract, beyond the lining and also in adjacent organs can be done directly.

According therefore to the present invention there is provided a method of examining a gastro intestinal tract comprising inserting a probe having an ultrasound transducer array into the tract, providing a fluid medium between the array and the lining of the tract to couple the array and the lining, and energizing the array to produce an ultrasound image of the tract.

According to a further aspect of the present invention there is provided a probe suitable for use in internally inspecting a gastro intestinal tract comprising a head connected to a flexible cable, an ultrasound array mounted on the head, the array including a plurality of transducers circumferentially spaced around the head, and transmitting means to transmit signals from the transducers to a processing device to produce an image.

An embodiment of the invention will now be described by way of example only with reference to the accompanying drawings in which.

Figure 1:
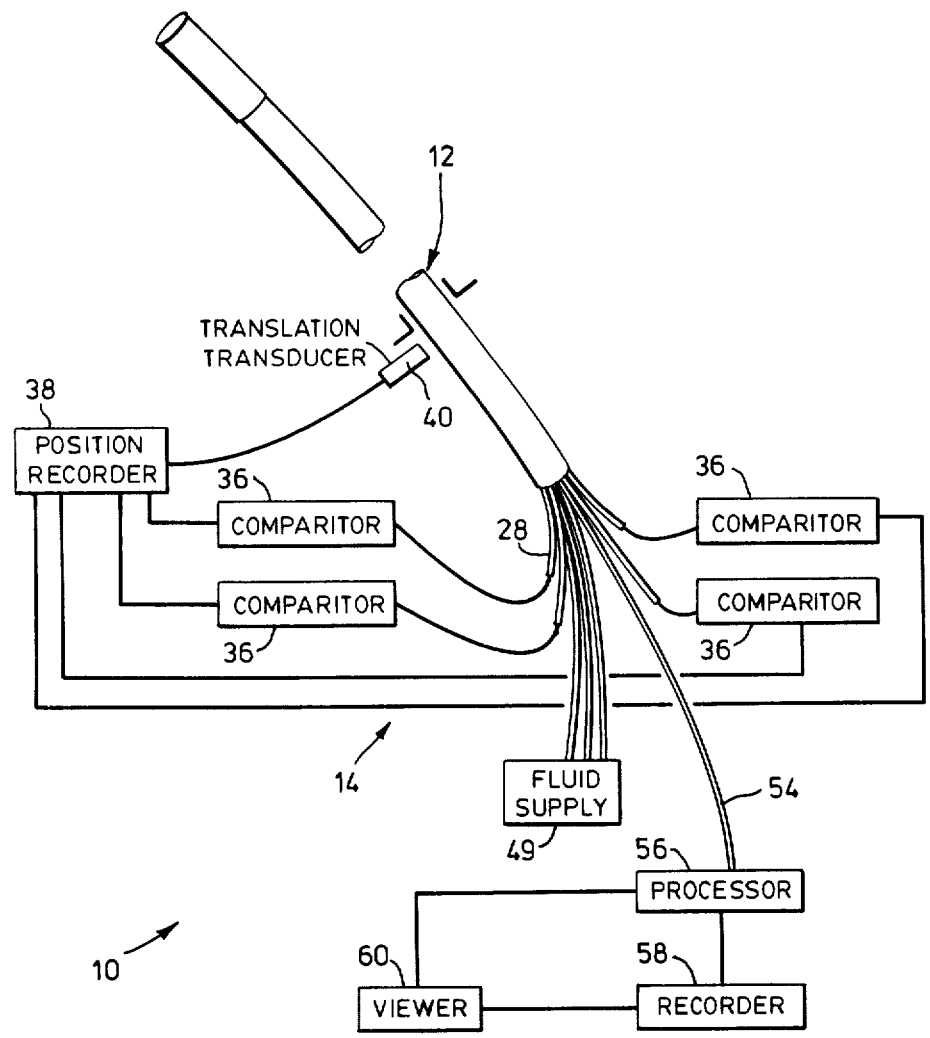
FIG. 1 is a diagrammatic representation of apparatus for examining a gastro intestinal tract.
Figure 2:
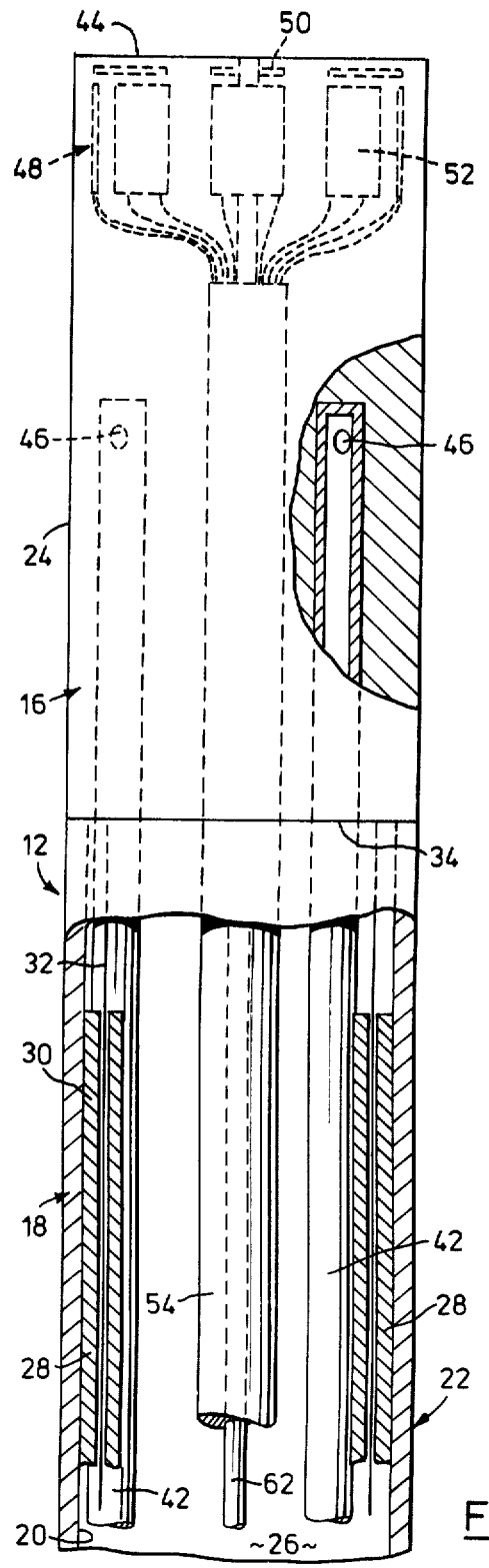
FIG. 2 is an enlarged view of a portion of the apparatus shown in FIG. 1 with portions of the apparatus sectioned for clarity.
Figure 3:
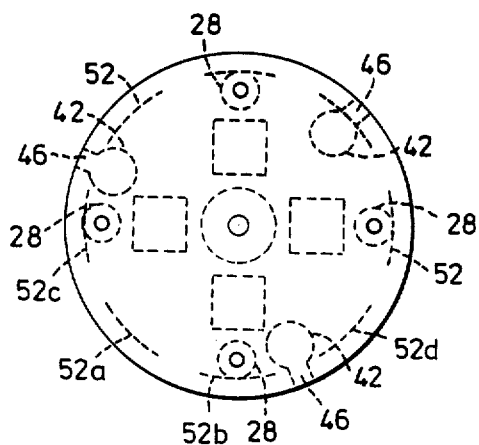
FIG. 3 is a plan view of the apparatus of FIG. 2.
Figure 4:
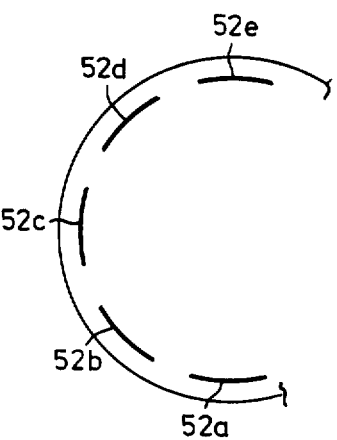

Referring now to the drawings, an examination apparatus 10 includes a probe 12 and processing apparatus generally designated 14. The construction of the probe may best be seen in FIGS. 2 and 3 and includes a head 16 and a body portion 18. The body portion 18 is formed from an elongate tube 20 which is flexible in a direction transverse to its longitudinal axis, but sufficiently stiff to enable the probe to be pushed along the gastro intestinal tract. The tube 20 has continuous peripheral wall 22 which smoothly merges with an exterior surface 24 of the head 16. The head 16 incorporates two ultrasound crystal arrays 48, 50. The array 48 includes a number of ultrasound crystals 52 which are circumferentially spaced around the head 16 to produce a sound image of the portion of the tract surrounding the head 16. The arrays 48, 50 are electrically connected to miniature electronic circuits and to an electrical cable 54 which extends along the tube 20 to a processor 56. The processor 56 is operable to selectively energize each crystal 52 of the array 48 to produce a real time scan of the tract surrounding the head 16 and to process the signals received by the crystal into a condition to be recorded by a recorder 58. The image of the tract can then be viewed on a viewer 60. The crystals 52 are energized in sequence so that a real time scan is obtained. This scan consists of a number of contiguous sectors spanning 360°. Each sector is produced by appropriate temporal summation of the signals from several of crystals 52.

The array 50 which lies generally parallel to the end is also controlled by the processor 56 to produce an image of the tract immediately in front of the head 16. This image may be viewed during advance of the probe 12 on the viewer 60 to enable the head 16 to be advanced in the appropriate direction.

The interior 26 of the tube 20 accommodates four cable assemblies 28 equally spaced around the wall 22 and each of which includes a sleeve 30 and a cable 32. The sleeve 30 is secured to the wall 22 and the cable 32 attached to an under surface 34 of the head 16.

The cable 32 may slide relative to the sleeve 30 to change the relative orientation of the head 16 and the body portion 18.

Each cable assembly 28 is connected at its lower end to a position adjustment and sensing device 36 which is operable in response to a manual input to move the cable relative to the sleeve and produce a signal indicative of the relative movement of the cable and sleeve. Each position adjustment and sensing device 36 is connected to a position recorder 38 which also receives a signal from a translation transducer 40. The translation transducer 40 detects the movement of the probe along its longitudinal axis so that the position recorder 38 is able to record the direction of movement of the head 16 by virtue of the position adjustment and sensing device 36 and the translation of the probe in that direction. This enables a representation of the path of movement of the probe, and consequently the shape of the gastro intestinal tract to be reconstructed.

The interior 26 of the tube 20 also houses three lumens 42 which are equally spaced about the axis of the tube and extend into the head 16. The lumens 42 terminate between an end surface 44 and the undersurface 34 are connected to the exterior surface 24 by a nozzle 46. The lumens 42 are connected to a fluid supply 49 which selectively supplies fluid to one or more of the lumens 42 for discharge through the respective nozzle 46.

A biopsy lumen 62 is accommodated in the head 16 on the longitudinal axis of the probe to permit sampling of material from the tract. In addition it could be used to remove local air pockets.

In operation, the probe 12 is advanced along the tract by viewing the image produced by the array 50 and manipulating the head during advancement. During such advancement the position recorder 38 records the movement of the probe along the tract to provide a record of the path of movement of the probe. During this time fluid is supplied from the supply 49 to the nozzles 46 and through the biopsy lumen 62 to achieve acoustical coupling for array 50.

The array 50 is also useful in determining the nature of an obstruction in the tract, the extent of such an obstruction, and, of course, the appropriate action to take.

When the probe 12 has reached the desired position in the tract, the array 48 is energized and fluid from the fluid supply 49 is directed along the lumens 42 and expelled from the nozzles 46 to provide a localized fluid environment. The fluid couples acoustically the crystals 52 and the tract wall and is provided intermittently as required to maintain the coupling and the image quality. The head 16 may be centered in the tract by selective supply of fluid to one of the nozzles 46 so that the head is moved by the impulse from the nozzle away from the adjacent tract wall.

The probe 12 is then withdrawn progressively and the image of the tract produced by the array 48 recorded. The output of the position recorder 38 may be recorded with the image of transducer array 48 to provide an indication of the location of the probe 12 within the tract corresponding to the image. Thus a correlation between the position recorder data and the image may be obtained.

It will be seen therefore that a three dimensional image of the tract and beyond extending to adjacent organs may be obtained and recorded for future consultation.

If desired, the position of the probe within a tract may be recorded by a radio transmitter integrally formed with the head and thereby avoid the necessity of the translation transducer, comparitors or position recorder. As a further alternative, the head 16 may be magnetically guided through the duct by external magnets placed around the body and selectively controlled to vary the orientation of the head 16. If completely independent passage of the probe 16 through the tract is required, the probe may be administered as a capsule with an integral power source. The data representing the images of the array 48 may be transmitted as a radio signal for reception outside the tract. In this instance, the coupling between the array 48 and the tract may be obtained by administering fluid with the capsule which will pass with the capsule through the tract.

An internal examination of the tract is, therefore, possible by use of the probe and by providing an acoustic coupling in the form of a localized fluid environment. This overcomes the problems associated with external ultrasound examination caused by gaseous pockets within the patient and enables accurate information to be recorded and reviewed as required.

What we claim as our invention is:

1. A probe suitable for use in internally inspecting a gastro intestinal tract and adjacent organs comprising a head connected to a flexible cable, first means on said probe to provide an image of the tract in advance of said probe, an ultrasound array mounted on said head and including a plurality of transducers circumferentially spaced around said head, transmitting means to transmit signals between said array and a processing device to produce an ultrasound image of said tract and fluid outlet means on said head to deliver fluid directly to said tract surrounding said head to acoustically couple said array to said wall and enable displacement of said probe along said tract whilst maintaining said acoustic coupling.

2. A probe according to claim 1 wherein said fluid outlet means includes a plurality of circumferentially spaced nozzles and an axial lumen to permit removal of localized air from said tract, to provide a forward fluid source and to accommodate a biopsy needle.

3. A probe according to claim 2 including means to vary the relative flow rate through said nozzles.

4. A probe according to claim 1 including manipulating means to vary the orientation of said head to said cable.

5. A probe as claimed in claim 1 wherein said first means to provide an image of the tract in advance of said probe comprises an ultrasound array mounted on a leading edge of said probe and connected by said transmitting means to said processing device.

6. A method of examining a gastro intestinal tract comprising the steps of inserting a probe having an ultrasound transducer array into said tract, energizing said array to provide an ultrasound image of the tract surrounding said probe, and acoustically coupling said array and the walls of said tract by supplying fluid from said probe directly into said tract to enable displacement of said probe along said tract whilst maintaining said image.

7. A method according to claim 6 including the further step of recording said image for subsequent reproduction.

8. A method of examining according to claim 6 including the step of utilising means mounted on said probe to obtain an image of said tract in advance of said probe.

* * * * *